United States Patent
Zhou et al.

(10) Patent No.: US 6,649,130 B1
(45) Date of Patent: Nov. 18, 2003

(54) REACTION PROCESS IN HYBRID REACTOR FOR PROPYLENE AMMOXIDATION

(75) Inventors: Robert L. Zhou, Fox River Grove, IL (US); W. Patrick Dennler, Houston, TX (US); Anil R. Oroskar, Oakbrook, IL (US); Bipin V. Vora, Naperville, IL (US); Hayim Abrevaya, Wilmette, IL (US); Laurence O. Stine, Western Springs, IL (US)

(73) Assignee: UOP LLC, Des Plaines, IL (US)

( * ) Notice: Subject to any disclaimer, the term of this patent is extended or adjusted under 35 U.S.C. 154(b) by 501 days.

(21) Appl. No.: 09/635,953

(22) Filed: Aug. 10, 2000

Related U.S. Application Data

(62) Division of application No. 09/198,300, filed on Nov. 23, 1998, now Pat. No. 6,143,915.

(51) Int. Cl.[7] .............................. B01J 8/08; B01J 8/18; B01J 8/26; B01J 8/28; B01J 8/30

(52) U.S. Cl. ................... 422/146; 422/139; 422/140; 422/141; 422/142; 422/144; 422/145; 422/147

(58) Field of Search .................. 422/139, 140, 422/141, 142, 144, 145, 146, 147, 188, 189, 198, 200

(56) References Cited

U.S. PATENT DOCUMENTS

| | | | | |
|---|---|---|---|---|
| 3,844,973 A | * | 10/1974 | Stine et al. ................ 502/42 |
| 3,919,115 A | * | 11/1975 | Stine et al. ................ 502/42 |
| 3,953,175 A | * | 4/1976 | Pulak ...................... 422/144 |
| 4,152,393 A | * | 5/1979 | Callahan et al. .......... 422/144 |
| 4,246,191 A | * | 1/1981 | Pujado .................... 558/320 |
| 4,246,192 A | * | 1/1981 | Pujado .................... 558/320 |
| 4,340,566 A | * | 7/1982 | Thompson et al. ....... 422/143 |

OTHER PUBLICATIONS

New Developments in Selective Oxidation II, Second World Congress & Fourth European Workshop Meeting, Benalmadena, Spain, Sep. 20–24, 1993.*

Grasselli, Robert K., and Suresh, Dev D., The Standard Oil Company (Ohio) Research Department, Cleveland, OH "Aspects of Structure and Activity in U–Sb–Oxide Acrylonitrile Catalysts", Journal of Catalysis, pp. 273–291, 1972.*

(List continued on next page.)

*Primary Examiner*—Jerry D. Johnson
*Assistant Examiner*—Alexa A. Doroshenk
(74) *Attorney, Agent, or Firm*—John G. Tolomei; James C. Paschall

(57) ABSTRACT

A hybrid reactor arrangement provides a reactive design that achieves higher acrylonitrile yield and lower catalyst circulating rate. The hybrid reactor design first passes a mixture of reactants and catalyst through a circulating bubbling bed reaction section. Heat exchange coils or other cooling medium in the bubbling bed reactor section maintain temperature in a range that will maximize the selectivity of reactants to the acrylonitrile product. The bubbling bed reactor section provides the initial conversion of the reactant. A circulating fluidized bed reaction zone finishes the conversion of reactants to a high yield under conditions that reduce the occurrence of secondary reactions that could otherwise produce unwanted by-products. The circulating fluidized bed reactor section maintains nearly plug flow conditions that allow continued conversion of unreacted feed components through primary reactions while limiting the time for secondary reactions to continue and diminish the final yield of products. Selectivity and conversion may also be improved by sequential addition of oxygen into the CFB reaction section. The sequential addition of oxygen may occur by the direct injection of an oxygen-containing gas or by the delivery of re-oxidized catalyst particles that are fully recharged with the lattice oxygen necessary for the reaction. Through this method the hybrid reactor provides the typical 5% improvement of higher acrylonitrile product yield from CFB-type reaction zones while reducing the required catalyst circulation by a factor of 10 or more.

11 Claims, 6 Drawing Sheets

OTHER PUBLICATIONS

Dai, Q. L. et al., "Reaction Network and Kinetic Model of Ammoxidation of Propylene to Acrylonitrile," UNILAB, Zhejiang University Branch, Hangzhou, Peoples Republic of China, Huaxue Fanying Gongheng Yu Congyi (1993), 9,(4), pp. 345–352.*

"Effect of Hydrodynamic Conditions in an Industrial Scale Fluidized Bed Reactor on Selectivity and Yield in Acrylonitrile Preparation by Ammoxidation of Propene", paper by Chemische Technik 48 (1996).*

Chen, B.H., Dai, Q.L., and Lu, D. W., "Development and Modeling of a Loop Fluidized Bed Reactor with Baffle for Propylene Ammoxidation", Department of Chemical Engineering, Zhejiang University, Peoples Republic of China, Chemical Engineering Science, vol. 51, No. 11, Elsevier Science, Ltd., Great Britain, pp. 2983–2988, 1996.*

* cited by examiner

REACTION PROCESS IN HYBRID REACTOR FOR PROPYLENE AMMOXIDATION

CROSS-REFERENCE TO RELATED APPLICATION

This application is a Division of application Ser. No. 09/198,300 filed Nov. 23, 1998, now U.S. Pat. No. 6,143,915 the contents of which are hereby incorporated by reference.

FIELD OF THE INVENTION

This invention relates generally to the control of temperatures and selectivity in reactors that circulate catalyst. This invention also relates to processes for reactions that use a particulate catalyst as an oxygen carrier through reversible oxidation-reduction. This invention can also relate specifically to the production of acrylonitrile by the ammoxidation of propylene in the presence of a particulate catalyst.

BACKGROUND OF THE INVENTION

Processes that contact reactants with circulating catalyst particles in a reaction zone are well known. One of the most well known processes that contacts reactants and regenerants with circulating catalyst particles is the fluidized catalytic cracking (FCC) process for the conversion of heavy hydrocarbons. U.S. Pat. No. 3,844,973 shows a regenerator arrangement used to regenerate catalyst in an FCC process that has a first dense bed that supplies catalyst to a relatively dilute phase catalyst mixture in a superadjacent transport riser. U.S. Pat. No. 3,919,115, U.S. Pat. No. 3,953,175, and U.S. Pat. No. 4,340,566 shows a variety of additional FCC regenerator arrangements that operate with a relatively dense phase bed and that supply catalyst particles to a relatively dilute phase transport riser.

Processes for the ammoxidation of propylene to produce acrylonitrile are generally well known. U.S. Pat. No. 4,246,191 provides an extensive list of references and specific descriptions of various patents that describe different methods of contacting reactants for the production of acrylonitrile with particulate catalyst for carrying out the ammoxidation reaction. U.S. Pat. No. 4,246,191 is particularly directed to temperature control of particulate catalyst in a fixed bed reaction zone having a top bed surface that extends close to the inlets of devices for the separation of catalyst from the acrylonitrile products. Control of the temperature in the particle bed minimizes the temperature deviation along the reactor profile.

The ammoxidation of propene to produce acrylonitrile is generally believed to be a redox process and that lattice oxygen from circulating solids can supply oxygen to the reaction. It is also known that lattice oxygen can be regenerated by air at certain temperature ranges. U.S. Pat. No. 4,152,393 discloses a reactor design for circulating catalyst from a first fluidized bed for the ammoxidation of propylene to produce acrylonitrile and a second bed for the regeneration of the catalyst. The arrangement continuously circulates catalyst from one bed to another and isolates the fluids from each individual bed to prevent intermixing. U.S. Pat. No. 4,246,192 teaches the oxidative regeneration of catalyst for the ammoxidation of olefins by the taking of a small stream of catalyst from a reaction zone for the ammoxidation of olefins. In this arrangement catalyst transfer lines connect the regeneration zone and reaction zones in this arrangement.

The ammoxidation reaction may also be carried out without a separate regeneration zone in which case oxidation of the catalyst material occurs within the reaction zone. Typically, a stoichiometric excess of oxygen in relation to the feed gas will be sent to the ammoxidation reaction zone.

Single bed reactors for the ammoxidation of propylene to produce acrylonitrile have been generally preferred. In particular the fixed bubbling bed type have been preferred to reduce the volume of catalyst circulation required in conventional transport-type arrangements for ammoxidation of propylene (see page 14 of "New Developments in Selective Oxidation II", Proceedings of the Second World Congress and Fourth European Workshop Meeting, Benalmadena, Spain, Sep. 20–24, 1993). The use of multiple beds of the same type, again the bubbling bed variety, is disclosed in a paper by the Chemische Technik 48 (1996) entitled "Effect of Hydrodynamic Conditions in an Industrial Scale Fluidized Bed Reactor on Selectivity and Yield in Acrylonitrile Preparation by Ammoxidation of Propene".

The ammoxidation of propene typifies heterogeneous catalytic reactions that evolve large amounts of heat, but require a relatively narrow range of temperature to be maintained as the reactants contact the particulate catalyst in order to inhibit secondary reactions that produce unwanted by-products. In the case of ammoxidation the reaction is very exothermic and continued reaction can further oxidize the product into nitrogen and carbon oxides when in the presence of oxygen. As demonstrated by the prior art, reactors for ammoxidation of propylene to produce acrylonitrile are well known. The current reactor configuration favored for most commercial arrangements is a bubble fluidized-bed reactor. The superior heat transfer characteristics of the bubble fluidized-bed reactors have led to their wide spread acceptance for ammoxidation. The reactor removes the reaction heat from the ammoxidation reaction efficiently by installing a heat transfer device inside the reactor.

A long standing problem with the use of a bubble fluidized-bed reactor is the relatively low superficial gas velocity that can be maintained through the reactor while still operating in a dense phase condition. Superficial gas velocity through the bed must be restricted to around 0.5 m/s. These low velocities present serious back-mixing problems within the reactor that randomly changes residence time and overall lowers the selectivity of the process to the desired product.

One solution for reducing the degree of backmixing has been a circulating fluidized bed (CFB) reactor. This reactor reduces the degree of gas mixing by passing reactants and catalysts to a transport conduit such as a riser-type reactor. Such reaction arrangements promote careful control of reaction times and generally approach a plug-flow contacting of reactants and catalyst particles. A draw back to the CFB-type reaction arrangement is the removal of heat. Heat transfer devices are typically not suitable for use within the circulating particulate catalyst environment. The provision of a heat exchange surface in a CFB-type reaction zone also leads to catalyst attrition as well as presenting poor heat transfer conditions due to the relatively low density of the catalyst contained therein. Therefore, reaction heat has to be removed from the reactor by circulating catalyst to avoid any large temperature increase which, again, will result in a higher yield of undesired by-products such as carbon dioxide. Typically, such reactors require a high catalyst circulation rate to maintain low temperature increases in the reactor. For example, a typical CFB-type reactor must circulate about 800 kg of solid catalyst for each kg of acrylonitrile that is produced to keep the temperature increase below about 10° C. as the catalyst and reactant mixture passes from the inlet to the outlet.

It is known from EP 0 189 261 A1 to use the combination of a bed-type reaction zone below a riser-type reaction zone for the production of maleic anhydride. EP 0 189 261 A1 also discloses that a metal oxide may serve as a carrier for a significant portion of the stoichiometrically required oxygen through rapid and reversible oxidation-reduction. However, EP 0 189 261 A1 teaches, in conjunction with its examples for maleic anhydride production, that riser reaction zones, fluidized bed reaction zones, and combinations thereof have no particular advantage over each other.

Therefore, it is an object of this invention to increase selectivity for acrylonitrile by reducing the backmixing inside a particle contact-type reactor.

It is another object of this invention to lower catalyst circulation in a CFB-type reactor arrangement for the production of acrylonitrile.

It is a further object of this invention to control oxidation reactions that take place within a typical ammoxidation reaction.

It is a yet further object of this invention to improve the selectivity of acrylonitrile generated from an ammoxidation reaction.

It is another object of this invention to improve the mixing of oxygen that enters the ammoxidation reaction zone.

SUMMARY OF THE INVENTION

These objectives are achieved by a hybrid reactor arrangement that provides dual reaction zones which simultaneously increase the acrylonitrile yield and reduce the production of undesired by-products by improving the selectivity of the process to acrylonitrile production and lowering the catalyst circulation rate. The hybrid reactor has a bubbling fluidized-bed reactor in one section and a circulating fluidized-bed reactor in another section. The hybrid reactor efficiently removes heat in the bubbling fluidized-bed reactor section and completes the final conversion of reactants in a CFB reaction zone that reduces backmixing. Further selectivity and temperature control may be provided by staging the introduction of an oxygen-containing reactant into the CFB reaction zone. Together the two reaction zones improve the selectivity of acrylonitrile from the ammoxidation reaction.

This invention provides the necessary temperature control for sustaining the desired selectivity to production of acrylonitrile in the ammoxidation process. To achieve high selectivity the temperature must be high enough to sustain activation of the material and dispersion of oxygen from the lattice of the oxygen-supplying material. At the same time, temperature is often restricted to prevent molecular oxygen from producing unwanted by-products by reaction with reactants or products.

As a result, this invention combines the best of a conventional bubbling fluidized-bed with a CFB bed reactor to improve yield and selectivity while reducing the required catalyst circulation rate. The bubbling fluidized-bed contains a heat transfer device that removes the reaction heat from the bottom and maintains isothermal or nearly isothermal conditions within the bubbling fluidized-bed reactor. On average, the reaction zone of this invention can raise the yield of acrylonitrile by 5% or more from that obtained by complete bubbling fluidized-bed reactor when operating at a propylene conversion rate of about 98% in an ammoxidation reaction for the production of acrylonitrile. At equivalent conversions and selectivity, the hybrid reactor of this invention can reduce catalyst circulation by about ten-fold over that required to obtain similar yields from a CFB reactor arrangement.

The flow regimes within the different portions of the hybrid reactor are important elements of this invention. Fluidized conditions within the bubbling fluidized-bed portion of the reactor typically include a catalyst holdup of at least 25% and a superficial velocity that normally does not exceed 1 meter per second. Catalyst holdup is the ratio of the bulk volume of the catalyst contained in a vessel to the volume of that vessel. A majority of the initial conversion of the entering hydrocarbon feed will occur in the bubbling fluidized-bed portion of the reactor and, more typically, from about 60 to 70% of a conversion of propylene will be achieved in the bubbling fluidized-bed portion of the reactor. During operation, it is also important that the bubbling fluidized-bed temperature be carefully controlled. Typically, indirect heat exchange with an appropriate cooling fluid will maintain the bubbling fluidized-bed portion of the reactor at the desired temperature.

After initial reaction in the bubbling fluidized-bed portion of the hybrid reactor, reactants will pass from the bubbling fluidized-bed portion into the CFB portion of the hybrid reactor at a temperature controlled by the prior dense bed heat exchange and reaction. In most arrangements, the bubbling fluidized-bed is located below the CFB reaction section and the catalyst and reactants move upwardly through a riser-type transport conduit to achieve another 30 to 40% of the reaction under reaction conditions that approach plug-flow contacting. In a typical flow regime for the CFB reaction section, the catalyst holdup will not be greater than 15% and the superficial fluid velocity will not drop below 3 m/s. With this type of arrangement, the circulation ratio of solid catalyst to acrylonitrile produced can be reduced to 100 or less. Since most of the reaction heat has been removed from the bottom part, the remaining conversion that occurs in the top part of the CFB reactor can be controlled with only a fraction of the former catalyst circulation rate that was necessary to control reaction temperatures when using the CFB reactor alone.

The primary reaction for the production of acrylonitrile consumes significant amounts of oxygen. Typically, an air stream supplies these reactants. Staged injection of the oxygen input stream to the CFB reaction section can further improve the selectivity of the reaction. In another aspect of this invention, an oxygen-containing stream, typically air, is injected at a plurality of points along the length of the CFB reaction section. Whether in gas phase or bound in a carrier material, staged oxygen injection overcomes a primary difficulty of introducing air or any oxygen-containing stream into the reaction zones which can result in a mal-distribution and locally high temperature excursions within the bubbling or circulating fluidized-bed of catalyst particles.

Staged introduction of lattice bound oxygen into either reaction zone may provide further control of temperatures within the hybrid reactor. Controlling the utilization of lattice oxygen in the ammoxidation reaction zone reduces the temperature rise resulting from the oxidation reactions since the heat generated during the oxidation of the catalyst can be removed in the regenerator. This invention can inject the oxygen carrier material instead of gas phase oxygen into the reactor. Staged introduction of the lattice bound oxygen can increase the reaction selectivity since non-selective gas phase oxidation is avoided. Furthermore, staging the introduction of particulate material and its bound oxygen at several locations along the CFB reaction section can provide a more uniform oxygen supply than side injection of gas phase oxygen. More uniform oxygen supply benefits product selectivity. Poor mixing that may result from the side injection of oxygen gas can produce some local zones of high oxygen concentration that degrade product selectivity. In this manner, the amount of gas phase oxygen at the bottom of the bubbling fluidized-bed reaction section can be reduced far below the stoichiometric amounts required for ammoxidation and the remaining part may be supplied to the hybrid reactor through a catalyst that serves as a source of lattice oxygen.

Once depleted in lattice oxygen, the catalyst may be readily regenerated by oxidation with another source of oxygen. Regeneration via oxidation may take place in a separate regenerator. Furthermore, the regeneration zone may also serve as a nitrogen generator by isolated recovery of the oxygen-depleted gas stream from the regenerator.

Accordingly, in one embodiment, this invention is a process for the ammoxidation of propylene to produce acrylonitrile. The process contacts reactants with an ammoxidation catalyst at propylene ammoxidation conditions. In the process, reactants such as propylene and ammonia contact the ammoxidation catalyst in a dense phase reaction zone. The dense phase reaction zone maintains a dense bed of catalyst at fluidized conditions, including a catalyst holdup of at least 25% at a superficial gas velocity not exceeding 1.0 m/s. Indirect heat exchange with a cooling fluid cools the dense bed. An intermediate reaction stream from an outlet end of the dense phase reaction zone along with an oxygen source pass into a circulating fluidized bed (CFB). The intermediate reaction stream contains unreacted propene. The ammoxidation of propene continues as the intermediate reaction mixture passes through the CFB reaction zone and while a catalyst holdup not greater than 15% and a superficial gas velocity of at least 3 m/s are maintained in the CFB. As a result, a reacted stream containing acrylonitrile is recovered from the CFB.

In an apparatus embodiment, this invention is an apparatus for controlling the temperature and for limiting the backmixing of catalytic reactions. The components of this apparatus are a first and a second vessel, an indirect heat exchange surface, a reducer, at least one injector, at least one separator, and a separator outlet. The first vessel defines a dense phase reaction zone having a first transverse area and at least one reactant inlet. The at least one reactant inlet receives a plurality of reactants. An indirect heat exchange surface on the interior of the first vessel indirectly cools the dense bed reaction zone. A second vessel defines a circulating fluidized bed (CFB) reaction zone having a second transverse flow area less than the first cross-sectional flow area and a reactant outlet. A reducer joins an outlet end of the first vessel with an inlet end of the second vessel and establishes a reactant and catalyst flow path from the first vessel through the reducer and the second vessel and then out of the reactant outlet. At least one injector introduces a reactant-containing stream into the reducer or the second vessel along the reactant and catalyst flow path. At least one separator communicates with the reactant outlet to separate catalyst particles from the reactant streams, and a separator outlet then delivers a reacted stream.

In a more specific apparatus embodiment; this invention is an apparatus for the ammoxidation of propene to acrylonitrile by contact with a particulate catalyst. This apparatus is composed of both a first and a second vessel, an indirect heat exchange surface, a reducer, an oxygen injector, a separator, and a separator outlet. The first vessel defines a dense phase reaction zone having a first transverse area and at least one reactant inlet. The reactant inlet receives propylene and/or ammonia reactants. Another inlet or the reactant inlet can receive air or oxygen. An indirect heat exchange surface on the interior of the first vessel indirectly cools the dense bed reaction zone. The second vessel defines a circulating fluidized bed (CFB) reaction zone having a second transverse flow area less than the first cross-sectional flow area and a reactant outlet. A reducer joins an outlet end of the first vessel with an inlet end of the second vessel and establishes a reactant and catalyst flow path from the first vessel through the reducer and the second vessel and then out the reactant outlet. At least one oxygen injector introduces an oxygen-containing stream into the reducer or second vessel along the reactant and catalyst flow path. At least one separator communicates with the reactant outlet to separate catalyst particles from the reactant stream, and a separator outlet delivers a reacted stream.

Additional objects, details, and embodiments of this invention are disclosed in the following detailed description of the invention.

DETAILED DESCRIPTION OF THE INVENTION

Figure 1:
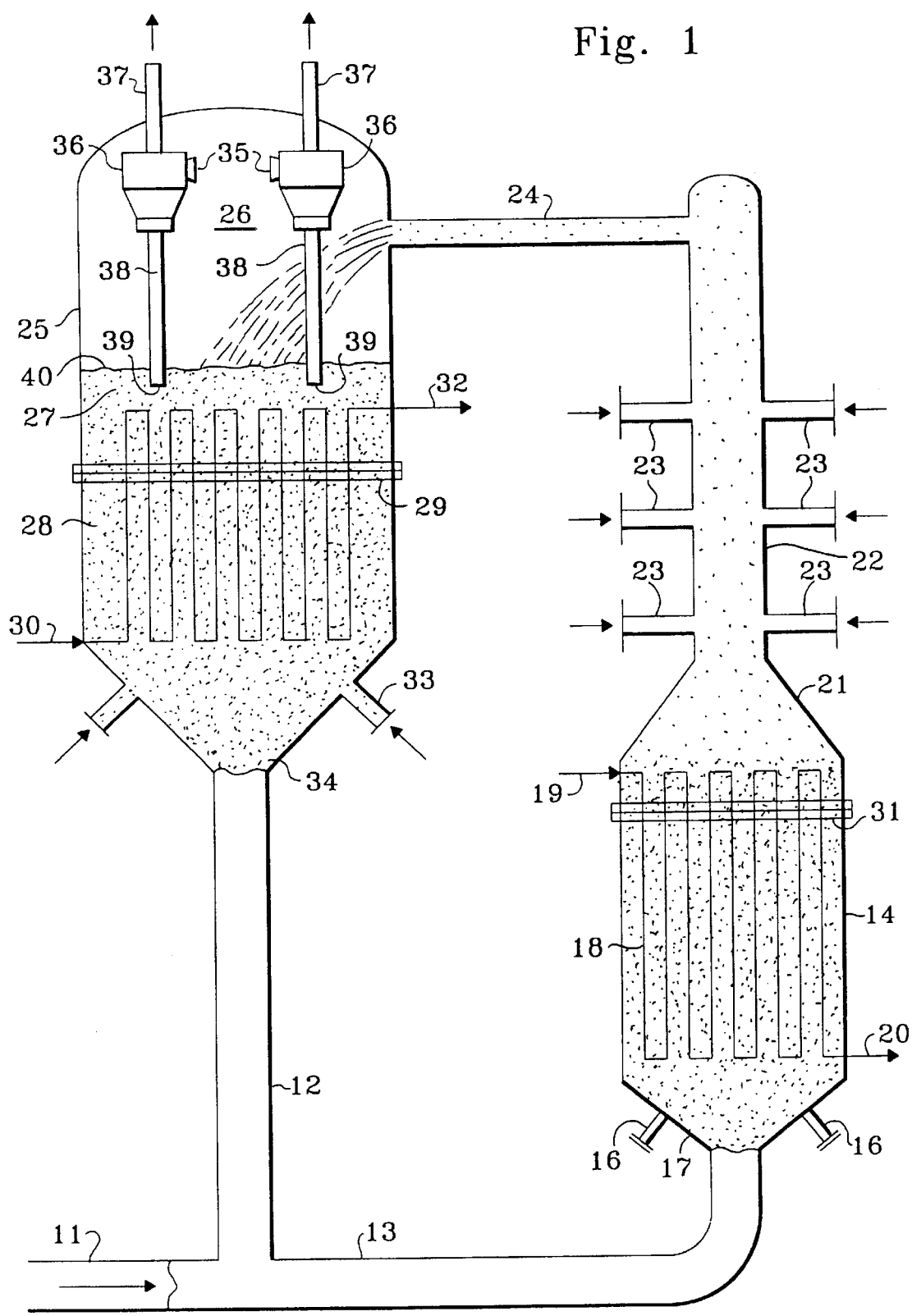
FIG. 1 is a schematic cross-section of a hybrid reactor for propylene ammoxidation

The invention is most useful for processes that seek to obtain high conversion of the hydrocarbon reactants. The most useful applications will be for conversions above 80 wt-% of primary reactants and, more typically, above 90 wt-% of primary reactants.

Oxygen is a primary reactant in the ammoxidation reaction. When using the hybrid reactor for the ammoxidation reaction, it is particularly beneficial to operate the bubbling bed section of the reaction zone with little excess gas-phase oxygen or even a stoichiometric deficient concentration of gas-phase oxygen. An important parameter for producing acrolein or acrylonitrile is the ratio of oxygen to the propene reactant. Preferably, this ratio will be maintained in a ratio of from 1 to 1.5. In the case of acrylonitrile production, the oxygen ratios will normally not exceed a molecular ratio of 2:1 and, more preferably, will lie at or below the stoichiometrically required ratio of molecular oxygen to hydrocarbon of 1.5. Preferably, mole ratio of molecular oxygen to hydrocarbons will be about 1.4.

The acrylonitrile process also uses a propene reactant. Pure and relatively impure olefin streams may provide suitable feed sources. Preferably the propene stream will be relatively pure and will have a propene concentration of 95 wt-%. If present, other feed impurities will typically comprise saturated and unsaturated hydrocarbons of the same or similar carbon number. Most olefin sources will comprise condensable gas streams. It may be particularly beneficial to integrate this process with catalytic or steam dehydrogenation processes for the production of the primary hydrocarbon reactants.

Another principal reactant in the ammoxidation is ammonia. The production of acrylonitrile or acrolein will depend on whether ammonia is present in the reaction zone. Without the presence of ammonia, only acrolein will be produced in any significant quantities. Typically ammonia at gas pipeline conditions or from an upstream ammonia plant are supplied to the process at a temperature of about 37° to 66° C. and a pressure of 7 bars or less.

Suitable catalysts for the bubbling bed reaction zone and the CFB reaction zone can comprise any particulate catalyst that promotes the desired ammoxidation reaction to which the hybrid reactor is applied. Catalysts as well as operating conditions and process arrangements are broadly described in U.S. Pat. No. 2,904,580, U.S. Pat. No. 3,230,246, U.S. Pat. No. 3,186,955, U.S. Pat. No. 3,197,419, U.S. Pat. No. 3,198,750, U.S. Pat. No. 3,200,081, U.S. Pat. No. 3,200,084, U.S. Pat. No. 3,446,833, U.S. Pat. No. 3,446,834, U.S. Pat. No. 3,686,295, and U.S. Pat. No. 3,892,794. Suitable catalyst for the process will generally comprise supported metal oxides. Bismuth molybdate oxides (U.S. Pat. No. 5,212,137, WO 95/05241, EP 0 573 713 B1), with small portions of other metals such as Fe or Te, are widely used in the industry. Per pass propylene conversion is about 98%, and the yield to acrylonitrile can be as high as 85%. Another type of catalyst system contains Fe-Sb-Te as the main ingredients (U.S. Pat. No. 4,826,802, U.S. Pat. No. 4,757,038, and U.S. Pat. No. 4,774,444). A complex of Mo and Sb oxides in conjunction with specific promoters such as Bi-V (U.S. Pat. No. 4,565,658) and Bi-Fe-U (U.S. Pat. No. 4,504,420) are also used in the manufacture of acrylonitrile.

The selective oxidation reactions in the ammoxidation process benefit from the use of the hybrid reactor in the consumption of both molecular oxygen and lattice oxygen. As generally accepted in the art, the primary consumption of molecular oxygen within such reaction zones operates to replace depleted lattice bound oxygen while the primary reaction path depletes oxygen by reacted lattice bound oxygen. An essential part of catalytic mechanism for these reactions is a supply of lattice oxygen from the catalytic material. It is known that the lattice oxygen often comprises two types: selective and non-selective. The selective or labile oxygen favors the production of acrolein or acrylonitrile while the non-selective lattice oxygen typically produces carbon oxides or waste products. An important function of sustaining the reaction with these catalyst is the re-oxidation of the catalyst to provide lattice oxygen to the reaction. The computation of rate constants and oxygen supply rates to the lattice structure of the catalyst are more fully explained by Dai et al of the UNILAB, Zhejiang University Branch, Hangzhou, Peoples Republic of China, in the paper entitled "Reaction Network and Kinetic Model of Ammoxidation of Propylene to Acrylonitrile," Huaxue Fanying Gongcheng Yu Gongyi (1993), 9(4), pp. 345–52.

In the reaction mechanism, propene, ammonium, and hydrogen all reduce the catalyst for removal of lattice oxygen. Re-oxidation ordinarily requires the presence of air with the catalyst at temperatures approaching 460° C. Some oxygen replacement in the carrier material may occur outside the ammoxidation reaction section in a separate regeneration zone. The replacement rate of oxygen in the regeneration arrangement may limit the amount of oxygen replacement that may be accomplished during regenerative re-oxidation, but in any event, will serve to reduce the total amount of oxygen replacement that must occur in the reaction zone to sustain the high conversion activity of the reactants. The operation of a separate regeneration zone may also increase the range of permissible operating temperatures in the reaction zone.

Suitable temperatures for the process must usually fall within a range that is high enough to raise the activation energy for re-oxidation to escape or maintain the reaction at suitable activity levels. However, excess temperature causes a decrease in selectivity by promoting conversion of feed and product hydrocarbons to carbon oxides. As a result, optimum temperatures for the process usually fall in a range of from 400° to 500° C. and, more preferably, in a range of from 430° to 460° C.

Principal temperature control occurs in the bubbling bed section of the hybrid reaction zone. The preferred form of temperature control for the bubbling bed section is an indirect heat exchange surface. The indirect heat exchange surface may comprise tubular arrangements or plate and channel arrangements. The indirect heat exchange surface will preferably extend over a substantial portion of the bubbling bed reaction zone. High bed density and low superficial velocity conditions in the bubbling bed reaction zone will provide a high heat exchange duty and promote precise temperature control within the bubbling bed. Suitable heat exchange fluids will comprise any fluid having a sufficient heat exchange capacity to provide the necessary cooling in the reactor bed. Preferred heat exchange fluids are water. Where desirable high heat capacity heat exchange fluid such as molten salts and liquid metal may be used.

The bubbling-bed reaction section will typically have a larger diameter than the CFB reaction section. The intermediate process stream that has been reacted in the bubbling bed reaction zone will pass upwardly through a transition section that reduces the flow area to the cross-section of the CFB reaction section. Typically, the flow area of the CFB section will be at least 75% less than that of the bubbling bed section. In terms of diameter, the CFB section will usually have a diameter that is ½ to ¼ of the diameter of the bubbling bed section.

The change in the cross-sectional area to a large degree changes the flow regime from one reaction section to the next. With the larger cross-section area, the bubbling bed reaction zone will typically have a catalyst holdup in a range of from 25 to 40% and, more typically, a catalyst holdup of greater than 30%. The superficial gas velocity flowing into the bubbling bed section is usually in a range of from 0.2 m/s to 1.0 m/s. The reduction in diameter decreases the catalyst holdup in the CFB reaction section such that it is typically in a range of from 5 to 15% and, more typically, the catalyst holdup in the CFB reaction section will usually not exceed 10%. Similarly, the reduction in the cross-sectional area will raise the superficial gas velocity in the CFB reaction section to a range of from 3 m/s to 10 m/s.

The CFB reaction section is usually in the form of a transport conduit that can take on a variety of orientations and configurations. A transport conduit refers to the riser or the other place where the CFB reaction takes place. The transport conduit may be oriented to have downward, upward, or cross-flow through it. A U-shaped transport conduit may be used to increase the overall flow path through the CFB reaction section while maintaining a low overall elevation for the hybrid reactor. Most typically, the transport conduit will comprise a riser conduit located above the dense bed reaction zone and connected to the bubbling bed reaction zone via a frusto-conical cone that provides the cross-sectional area and diameter reduction between the reaction sections.

The process requires recirculation of catalyst after contact with the reactants. Typically, the catalyst is separated from the reactant stream as it exits the CFB reaction zone. The catalyst particles separated from the reactive stream ordinarily return to the dense phase reaction zone in admixture with the reactants of the reactant stream. A separation vessel (also referred to as a disengaging vessel) may collect the catalyst that is separated from the CFB reaction zone and disengage the catalyst from the fluid stream. The separation vessel may be separated from the CFB reaction zone or may contain the CFB reaction zone in the form of a reactor riser. In either arrangement, the reacted stream will ordinarily enter an upper portion of the separation vessel which provides an initial separation of the catalyst from the reactant stream. The separation vessel may also contain a dense bed of catalyst that may be beneficially cooled by indirect heat exchange with a cooling fluid to further control catalyst temperatures. As with the cooling and dense bed reaction zone, the cooling zone is typically steam.

The primary concern in selecting pressures is the efficiency for downstream separation and having the necessary pressure for the operation of separators and other fractionation equipment. The process will usually operate at a pressure of from 1 to 5 atmospheres.

Figure 2:
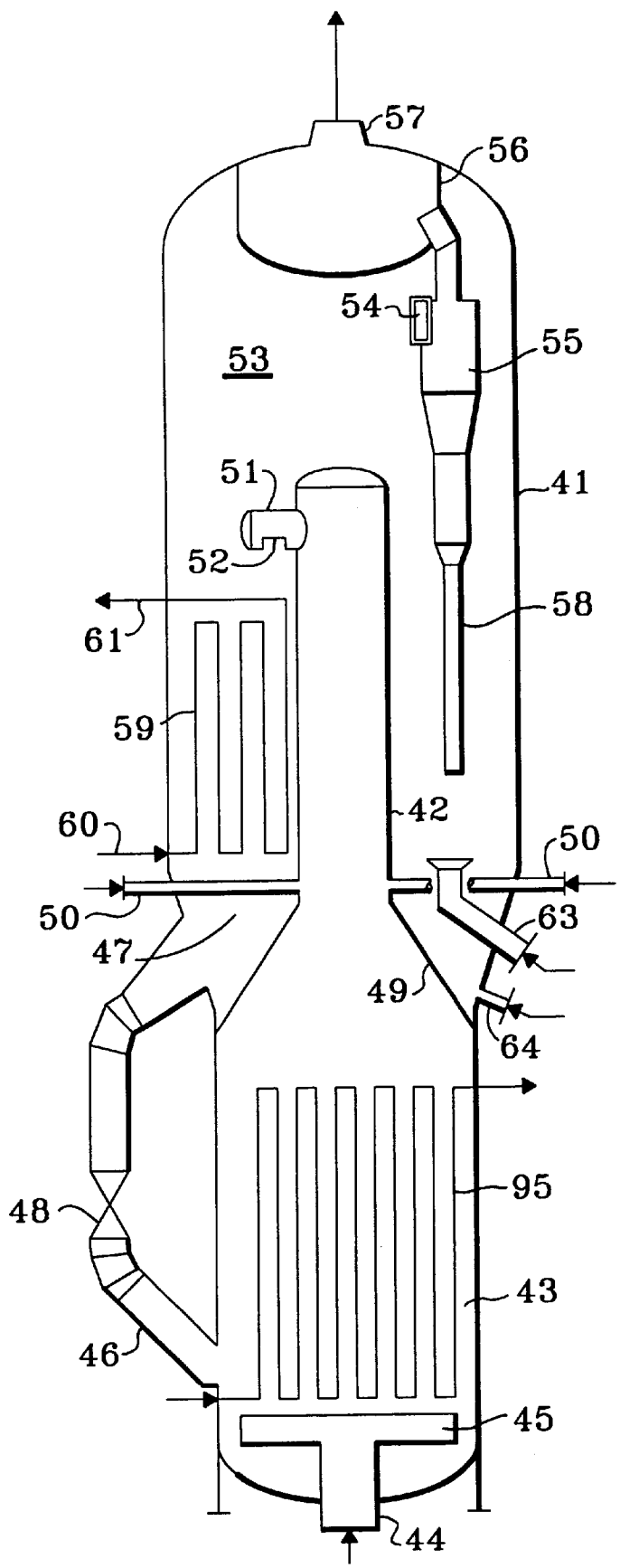
FIG. 2 is an alternate arrangement for the hybrid reactor shown in FIG. 1.
Figure 3:
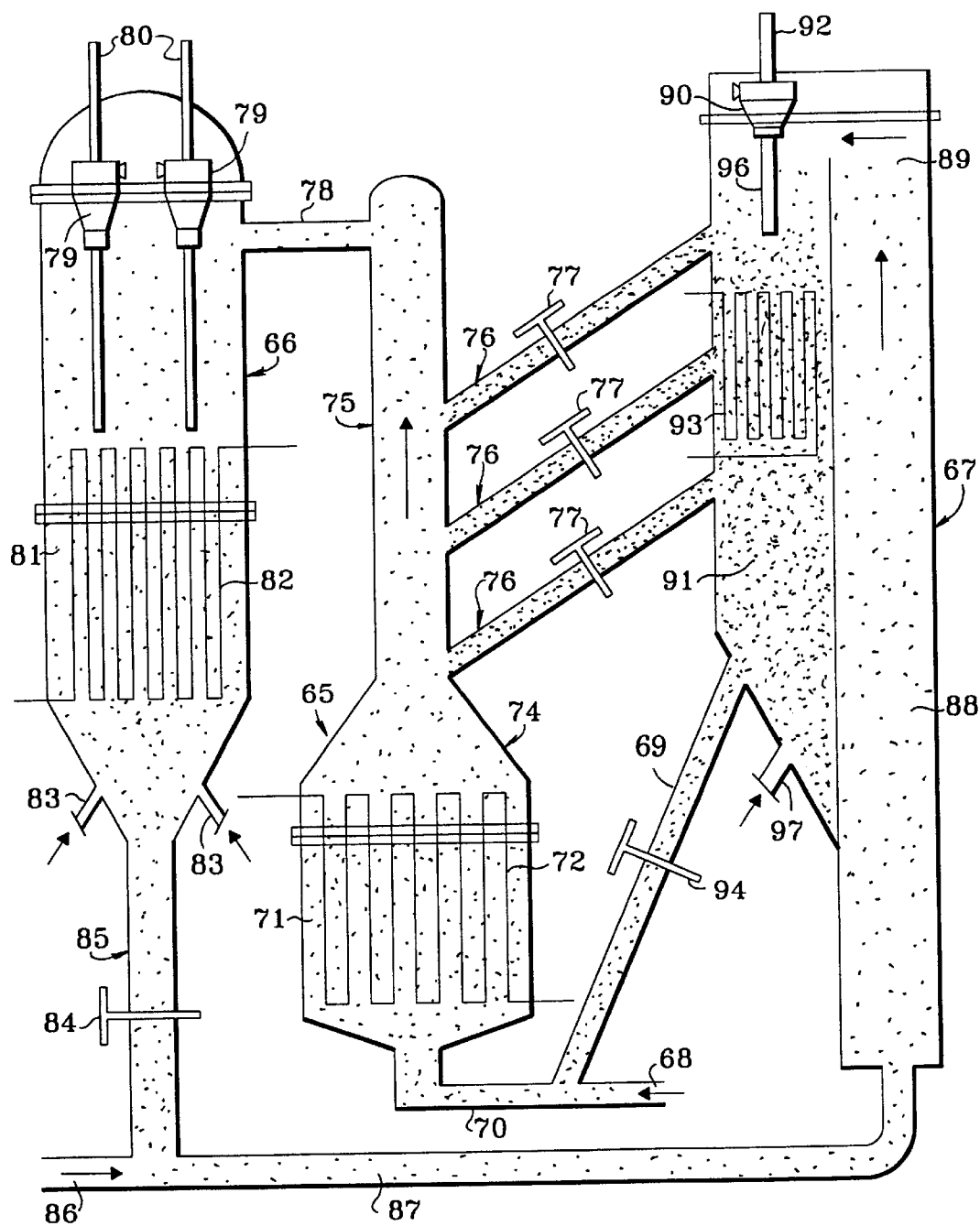
FIG. 3 is a schematic illustration of a hybrid reactor similar to that shown in FIG. 1 with the integration of catalyst re-oxidation and circulation.

Reference to FIGS. 1–3 may provide a more complete understanding of the process and apparatus of this invention. The figures are described in the context of a process for the production of acrylonitrile. The description of the figures in this context is for the purpose of explanation and illustration, but not for limitation.

FIG. 1 shows a feed mixture entering a hybrid reactor via a conduit 11. The feed mixture contains oxygen and propylene in an approximate molar/feed ratio of 1.4. The feed mixture entering conduit 11 also contains ammonia in a molar ratio of propylene of about 1.1. Solid catalyst flows downwardly through a conduit 12 into contact with the feed mixture at a catalyst/feed ratio of about 40. Mixing of the catalyst and feed mixture continues as it travels through conduit 13 on its way to a bubbling bed circulating reaction zone 14.

Bubbling bed circulating reaction zone 14 maintains the catalyst in a dense bed phase for initial reaction of the reactants and cooling of the reactants and to remove the heat produced thereby. The bottom of reaction section 14 may contain a distributor or other distribution device (not shown) to evenly spread the entering reactants over the bottom of the dense catalyst bed. Additional reactants or fluidization fluid may enter the bottom 17 of reaction section 14 via nozzles 16. Added reactants may comprise any of the primary reactants. Fluidization fluids may include inert material such as nitrogen which—in addition to fluidization—may provide supplemental means for temperature control.

FIG. 1 schematically shows an array of heat exchange tubes 18 that provide a contact surface for the indirect heat exchange with a coolant fluid that enters the coils via line 19 and leaves the coils via line 20. Suitable supports 31, shown schematically, maintain the position of the cooling coils 18 within the bed of reaction section 20.

Narrowing of the cross-sectional area from reaction section 14 via a reducer 21 raises the velocity of the upwardly moving fluid and decreases the catalyst density as it enters the circulating fluid bed (CFB) reaction zone 22. The bubbling bed reaction section usually operates at a stoichiometric deficit of oxygen. Oxygen may be added to the CFB reaction section in or anywhere above reducer 21. Staging of the oxygen injection, as shown in FIG. 1, by injecting it in a series of nozzles 23 over the length of the CFB reaction section provides improved distribution of oxygen and overall better selectivity to desired acrylonitrile products. Nozzles 23 serve as injectors for injecting the oxygen-containing fluid into the catalyst and reaction flow path at staged injection points along this length of the CFB bed. Overall residence time in the CFB reaction section will usually be in a range of from 5 to 10 seconds.

A transfer conduit 24 delivers the mixture of catalyst, products, by-products, and unreacted feed components to a separation vessel 25. The transfer conduit refers to the conduit connecting the CFB reaction zone and the separation vessel. Preferably, the transfer conduit discharges the mixture into an upper portion of separation vessel 25. The upper portion of separation vessel 25 ordinarily has a dilute catalyst density such that the discharge of the reacted mixture into the upper section provides an initial separation of fluids from the particulate catalyst. The particulate catalyst passes downwardly through a dilute phase section 26 and into a dense bed 27.

After initial separation by discharge from transfer to conduit 24, the fluid initially separated from the catalyst flows into inlets 35 of cyclone separators 36. Cyclone separators 36 provide a further recovery of catalyst from the separated product fluid and may be any type well known in the art. In the case of the production of acrylonitrile or acrolein, the reactants will be principally in a gas phase. However, suitable separators may accommodate liquid phases as well when the fluids entering the reactor are mixed phase or liquids.

Cyclone separators 36 produce a relatively catalyst-free output stream that exits the separation vessel 25 through outlets 37. Products may be recovered from the outlet stream exiting nozzles 37 through various methods known by those skilled in the art, but principally anticipated to be fractionation or other phase separation for the removal of unreacted feed components as well as other ancillary fluid streams that may be contained in the outlet streams.

The cyclone separators return recovered catalyst to the separation vessel through dip pipe conduits 38. Dip pipe conduits 38 will usually submerge their outlets 39 below the surface 40 of dense bed 27 to maintain a head of catalyst in the dip pipe conduits 38 and to provide a gas seal to prevent back flow of reacted fluids into dense bed 27.

Dense bed section 27 may house indirect heat exchange elements and may provide additional fluid injection points. An indirect heat exchange surface in the form of a plurality of heat exchange tubes 28 are fixed in dense bed 27 by a support 29. A heat exchange fluid enters tubes 28 from an inlet 30 and exits from an outlet 32. Normally water enters through inlet 30 and steam exits through exit 32. A pair of nozzles 33 can be used to provide additional steam or other fluidization medium to the dense bed 27. In a preferred embodiment, the dense bed 27 may serve as a regeneration zone to re-oxidize the catalyst and additional oxygen may enter through nozzles 33. Whether oxidized or simply recirculated, the recovered catalyst from separation vessel 25 exits the bed through an outlet 34. Recovered catalyst exiting outlet 34 passes downwardly through conduit 12 having contact with the feed mixture as previously described.

FIG. 2 shows a compact design for the hybrid reactor where a separation vessel 41 surrounds the CFB reaction zone 42. In this arrangement, the feed mixture enters the bubbling bed circulating reaction section 43 through an inlet 44 of a distributor 45. Distributor 45 introduces the feed mixture over the entire cross-section of the bubbling bed reaction zone. Instead of entering the bubbling bed reaction zone with the feed mixture, a conduit 46 recycles recovered catalyst into the bottom of the bubbling bed reaction zone 43 from a dense bed section 47 of separation vessel 41 at a rate controlled by a particle control valve 48. An indirect heat exchanger 95 removes heat from catalyst in the bubbling bed reaction zone 43. A reducer section 49, again, increases the velocity of the fluids passing upwardly from bubbling bed section 43 while at the same time reducing the catalyst density to accelerate the catalyst into CFB section 42. A pair of nozzles 50 inject oxygen into the mixture of catalyst and reactants at the base of CFB reaction section 42. A separation device 51 in the form of an arm having a downwardly projected opening 52 provides an initial discharge of the catalyst and reactant mixture into the dense bed region of separation vessel 41. Fluid reactants pass upwardly into a dilute phase section. 53 and are taken up by an inlet 54 of a cyclone separator 55. A plenum chamber 56, provided to accommodate multiple cyclones 55, collects the recovered fluid outlet stream for discharge from the separation vessel 41 through a central outlet 57. A dip conduit 58 again returns catalyst recovered by cyclone separator 55 to the dense bed section 47 of separation vessel 41. Cooling coils 59 provide indirect heat exchange with the dense bed of catalyst maintained in separation vessel 41. Typically, water entering an inlet 60 will boil—at least in part—to produce a steam-containing stream that exits the cooling coil from an outlet 61. Steam may be injected into the dense bed of separation vessel 41 through a nozzle 63. Additional oxygen may also be injected for regeneration purposes into dense bed 47 through a nozzle 64.

The separate separation vessel or disengaging space, as shown in FIG. 1 or the space that exists about the outside of the riser in the arrangement of FIG. 2, may be used as an additional reaction space for other reactions. Since, possible feed streams for the process will include saturated feeds that may pass saturated components with the reactive components through the reaction zone, such additional reactions could include steam dehydrogenation of corresponding saturation hydrocarbons that might enter the process with the olefin feed.

It may be possible to conduct the regeneration within the separate vessel arrangement for the disengagement of catalyst as shown in FIG. 1. A more extensive catalyst regeneration zone is shown in FIG. 3. Integration of regeneration into the process to provide re-oxidized catalyst as a source of oxygen injection is schematically presented in FIG. 3. FIG. 3 shows a hybrid reactor arrangement 65, a separation vessel arrangement 66, and a re-oxidation section 67. Apart from the staged addition of oxygen, the hybrid reactor 65 operates in much the same manner as that previously described. The feed mixture enters the process through a conduit 68. Re-oxidized catalyst from a conduit 69 joins the feed mixture and undergoes further mixing as the catalyst and reactants pass through a conduit 70. Conduit 70 again delivers the feed and catalyst mixture to the bottom of the bubbling bed circulating reactor 71 that contains an indirect heat exchange surface, in the form of tubes 72, for controlling the temperature of the catalyst bed. Catalyst and gases from the top of bubbling bed reaction section 71 enter reducer 74 that accelerates the upward velocity of the mixture as it reduces the catalyst density prior to discharge of the mixture into a CFB reaction section 75. A series of catalyst conduits 76 deliver re-oxidized catalyst at staged injection points along the length of CFB reaction section 75 at rates controlled by particle control valves 77.

The transfer conduit 78 carries the reacted stream into the separation vessel 66 for initial separation by discharge into separation vessel 66 and final separation of particulate matter by cyclones 79. Overhead conduits 80 deliver the product-containing stream to other facilities for further separation and recovery of product components. Catalyst from cyclones 79 along with initially separated catalyst passes downwardly into a dense bed section 81 of separation vessel 66. Dense bed section 81 may contain an indirect heat exchange surface such as schematically represented tubes 82 and one or more nozzles 83 for injection of additional fluids into the catalyst collected in dense bed 81.

A particle control valve 84 regulates the delivery of separated catalyst particles through a regenerator supply conduit 85. A conduit 86 delivers an oxygen-containing gas such as air into contact with the particles from separation vessel 66. The particles and air undergo further mixing and initial regeneration as they pass through a regenerator mixing conduit 87. Regenerator mixing conduit 87 discharges the mixture of the oxygen-containing gas and catalyst particles into regeneration zone 88 of regeneration vessel 67.

Regeneration zone 88 can provide the most favorable temperatures for restoring lattice oxygen to the catalyst particles and is not restricted to operation at conditions that are best suited for the selective conversion of reactants and the selective production of desired products. Regeneration zone 88 will normally operate in a fast fluidized mode that maintains again a low catalyst density and a relatively high velocity of gases that transport the catalyst undergoing regeneration to an upper section 89 of regeneration vessel 67. Upper section 89 of regeneration vessel 67 has an increased cross-sectional area that reduces the superficial velocity of the gases passing upwardly through regeneration zone 88 The reduction in gas velocity causes an initial separation of catalyst particles that collect in a collection zone 91. Catalyst can further be regenerated in zone 91, which may be operated in either a smooth fluidization or a bubbling fluidization regime. At the same time, the heat from catalyst regeneration (oxidation) may be removed by an indirect heat exchange surface such as that schematically represented by tubes 93. The collection zone 91 may contain one or more nozzles 97 for injection of additional oxygen-containing gas such as air. The regeneration gas which is typically depleted in oxygen exits cyclone separator 90 through an outlet 92. Gases exiting from outlet 92 may be recovered for use in other process arrangements. In particular, when the oxygen-containing gas entering conduit 86 is air, conduit 92 can deliver a nitrogen enriched gas stream for use in conjunction with this process or other processing applications. A dip pipe 96 delivers the recovered catalyst to the distribution section 91. Distribution section 91 provides catalyst for the initial mixing of catalyst and feed components at a rate controlled by particle control valve 94 and provides re-oxidized catalyst at a number of different elevations through valves 77 to simplify the multi-stage injection of re-oxidized catalyst along the length of the CFB reaction zone.

Injecting the catalyst instead of the oxygen-containing gas at a variety of points provides better mixing of the entering oxygen with the relatively low density catalyst stream passing upwardly through the CFB reaction section. In addition, the particles, now fully charged with lattice oxygen, can more readily deliver oxygen for the reaction of any remaining unconverted feed components.

EXAMPLES

The benefits of the hybrid reactor for propylene ammoxidation to produce acrylonitrile was studied by modeling of the ammoxidation reaction in a conventional bubbling fluidized-bed reactor, a circulating fluidized-bed reactor, and a hybrid reactor. Reaction kinetic data and rate expressions for propylene ammoxidation were obtained for a Mo—Bi—O catalyst. The following reaction network was used for modeling the ammoxidation of propylene to produce acrylonitrile.

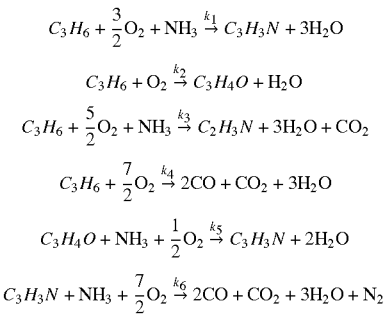

$$C_3H_6 + \frac{3}{2}O_2 + NH_3 \xrightarrow{k_1} C_3H_3N + 3H_2O$$

$$C_3H_6 + O_2 \xrightarrow{k_2} C_3H_4O + H_2O$$

$$C_3H_6 + \frac{5}{2}O_2 + NH_3 \xrightarrow{k_3} C_2H_3N + 3H_2O + CO_2$$

$$C_3H_6 + \frac{7}{2}O_2 \xrightarrow{k_4} 2CO + CO_2 + 3H_2O$$

$$C_3H_4O + NH_3 + \frac{1}{2}O_2 \xrightarrow{k_5} C_3H_3N + 2H_2O$$

$$C_3H_3N + NH_3 + \frac{7}{2}O_2 \xrightarrow{k_6} 2CO + CO_2 + 3H_2O + N_2$$

Rate constants for the primary and secondary reactions at various temperatures of operation of the kinetic model are listed in the following Table.

TABLE

|  | 415° C. | 430° C. | 440° C. | 450° C. | 465° C. |
| --- | --- | --- | --- | --- | --- |
| $k_1 \times 10^8$ | 102.57 | 129.22 | 158.34 | 188.45 | 242.74 |
| $k_2 \times 10^8$ | 6.908 | 12/22 | 18.55 | 26.54 | 46.16 |
| $k_3 \times 10^8$ | 5.05 | 6.21 | 6.65 | 7.35 | 9.09 |
| $k_4 \times 10^8$ | 2.00 | 3.19 | 3.50 | 4.72 | 7.63 |
| $k_5 \times 10^8$ | 9.56 | 12.24 | 22.31 | 30.9 | 37.99 |
| $k_6 \times 10^8$ | 13.80 | 23.27 | 32.76 | 45.92 | 75.30 |
| $k_7 \times 10^8$ | 8.68 | 73.42 | 113.03 | 165.84 | 274.33 |

Example I

Figure 4:
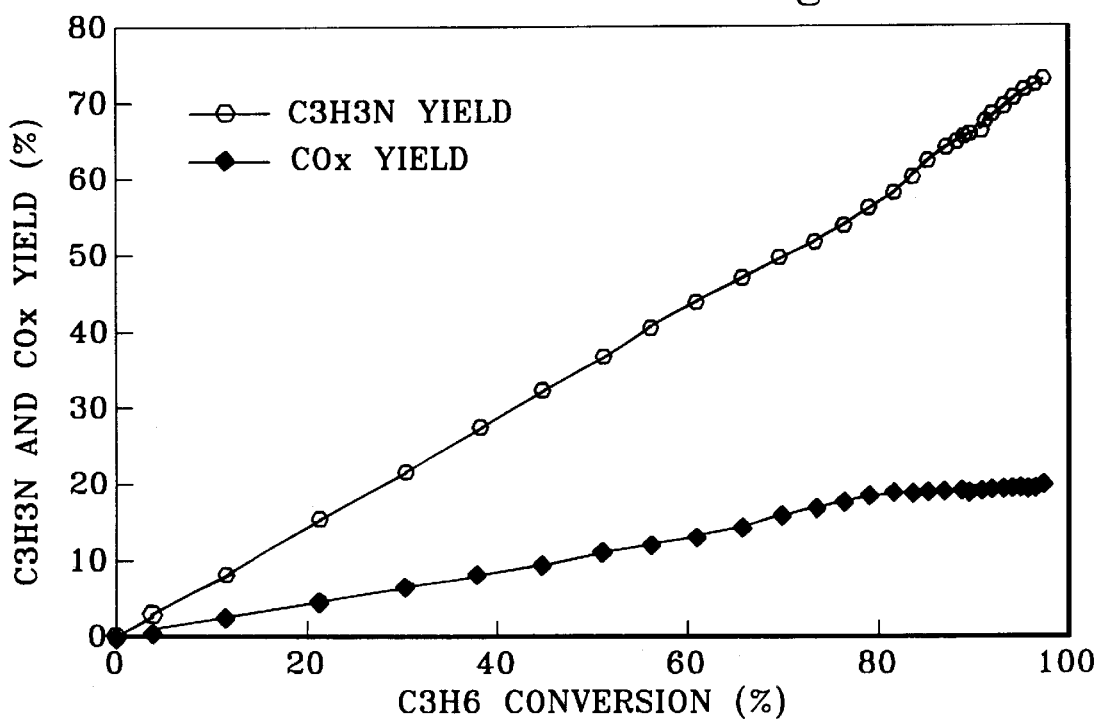
FIGS. 4–7 are plots showing the yield of primary products and by-products for various reactor configurations.
Figure 8:
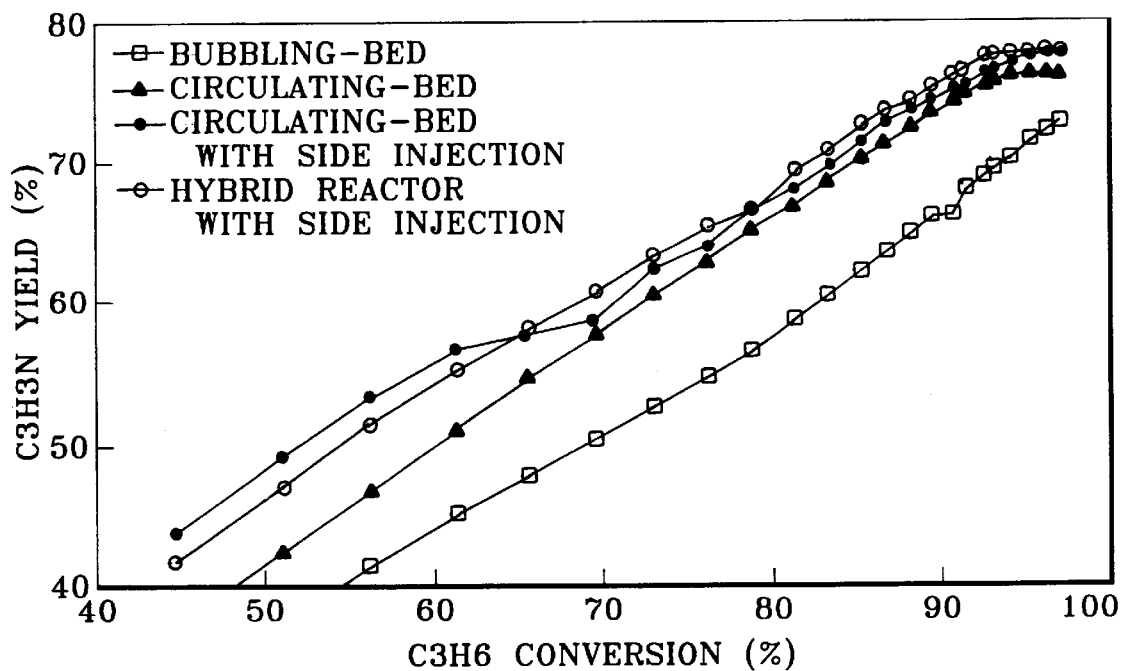
FIGS. 8 and 9 are graphs showing products and by-product yields respectively for the comparative operation of different reactor arrangements.
Figure 9:
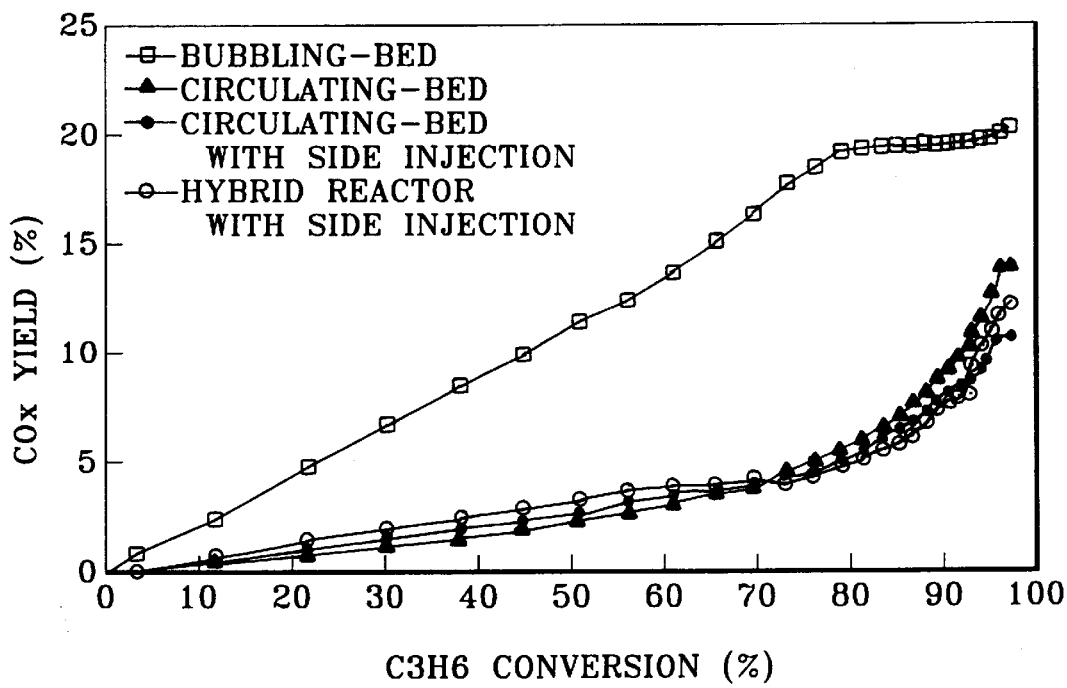

A bubbling fluidized-bed reactor was modeled using the above reaction kinetics. An isothermal reaction condition was applied since bubbling fluidized-bed reactors remove heat very efficiently. A heat transfer device was assumed inside the reactor to sustain the isothermal condition at a temperature of 430° C. FIG. 4 shows the yield of acrylonitrile and carbon oxides, including carbon dioxide and carbon monoxide, as a function of reaction conversion for the operation of the bubbling fluidized-bed reactor. Acrylonitrile is the major product and carbon dioxide and carbon monoxide are the undesired products of the propylene ammoxidation reaction. Other by-products such as acrolein, hydrogen cyanide, and acetonitrile are not shown in this figure and the subsequent figures since their concentrations fall far below those of acetonitrile and carbon oxides. FIG. 8 also contains the results of this modeling experiment and shows the acrylonitrile yield as a function of propylene conversions in a bubbling fluidized-bed reactor along with comparative data for the circulating fluidized-bed reactor and the hybrid reactor. FIG. 9 shows the carbon oxide yield for this modeling experiment along with the yield of carbon oxides in a bubbling fluidized bed, a circulating reactor and a hybrid reactor.

Example II

Figure 5:
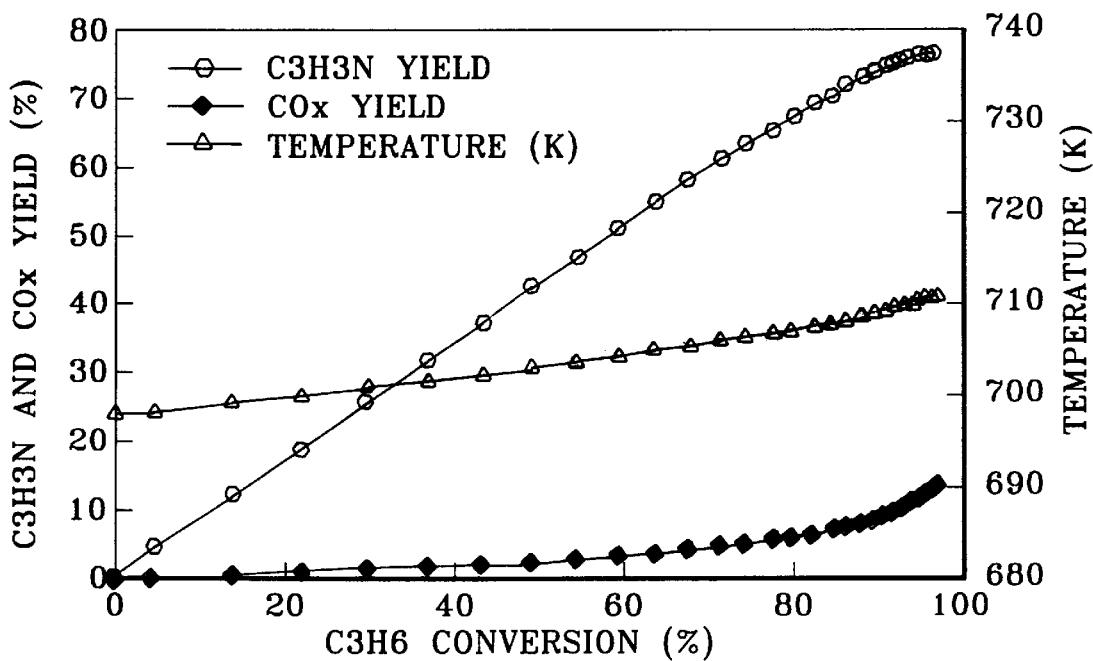
Figure 6:
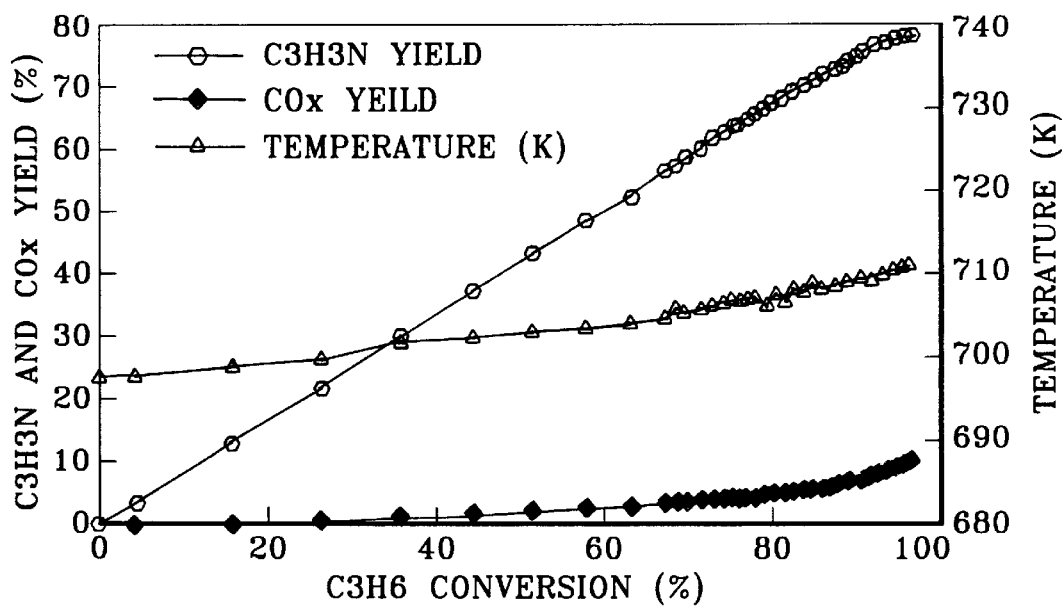

The circulating reactor was operated without heat exchange devices since it is normally not possible to install such devices inside the reactor. In addition, the heat transfer efficiency is very low since the catalyst density in a circulating reactor is low. Therefore, a non-isothermal condition was assumed for the circulating fluidized-bed reactor (CFB). FIG. 5 shows the yield of acrylonitrile and carbon oxides as a function of reaction conversion for the circulating reactor. The inlet temperature of the reactor is 430° C. Reactor temperatures are plotted in FIG. 5 and show a temperature increase along the reactor. The temperature rise is not significant since the circulating catalyst can carry away the heat. FIG. 6 shows a further improvement to the yield by introduction of the oxygen feed at four separate input points spaced evenly down the length of the CFB reactor. As mentioned, FIG. 8 shows the acrylonitrile yield as a function of propylene conversion in the circulating fluidized-bed reactor along with the other types of reaction zones in this comparative modeling. FIG. 8 demonstrates that the circulating reactor has a higher yield of the acrylonitrile than that of the bubbling reactor. The circulating reactor with side air (or oxygen) injection can have about 5% higher product yield of acrylonitrile than the conventional bubbling bed reactor. In order to achieve the product yield shown in FIG. 8 for a circulating reactor, the catalyst circulation rate will be 950 kg catalyst/kg acrylonitrile (based on 2500 kg/M$^3$ of catalyst density). FIG. 9 shows that the yield of carbon oxides is much higher in a bubbling reactor than that in a circulating reactor.

Example III

Figure 7:
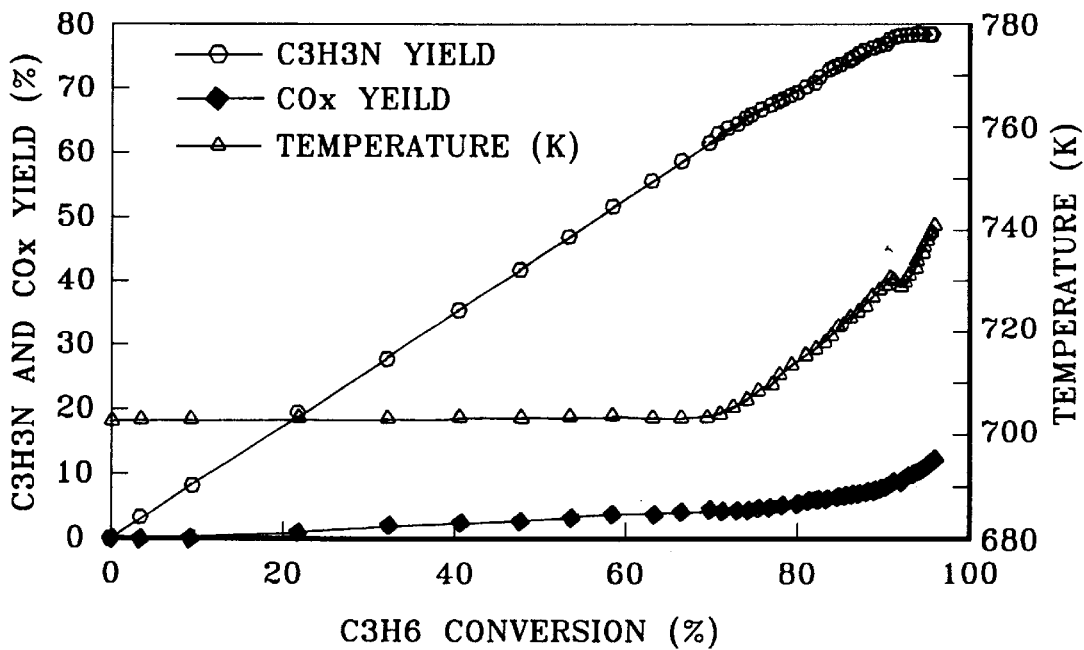

The model for the hybrid reactor again treated the reaction heat as removed by the circulating catalyst in the upper section and assumed a heat transfer device removed heat at the bottom part of the studied hybrid reactor. Hence, in the reactor model simulation, an isothermal condition was maintained at the bottom part of the hybrid reactor, and a non-isothermal condition was maintained at the top part of the reactor. Approximately 70% of the oxygen entering the hybrid reactor is injected at points spaced down the length of the circulating reactor section. FIG. 7 shows the yield of acrylonitrile and carbon oxide for the hybrid reactor and operating conditions. The oxygen stream was added to the CFB section of the reactor at three separate points spaced evenly down its length. Reactor temperatures are plotted in FIG. 7 for the hybrid reactor. The inlet temperature is 430° C. for the hybrid reactor and about a 40° C. temperature rise results along the circulating section of the reactor from the lower catalyst circulation.

As mentioned, FIG. 8 shows a comparison of the acrylonitrile yield as a function of propylene conversion in a bubbling fluidized-bed, circulating fluidized-bed reactor, and the hybrid reactor. It demonstrates that, like the circulating reactor, the hybrid reactor has a higher yield of the acrylonitrile than that of the bubbling reactor. Similar to the circulating reactor, the hybrid reactor with side air (or oxygen) injection can have about 5% higher product yield of acrylonitrile than the conventional bubbling bed reactor. Although the circulating reactor and the hybrid reactor have the similar product yield, the catalyst circulating rates for these reactors are different. To achieve the product yield shown in FIG. 8, the circulating reactor needed a catalyst circulation rate of 950 kg catalyst/kg acrylonitrile, which is about six and a half times higher than the rate of 146 kg catalyst/kg acrylonitrile that is needed in the hybrid reactor for the same product yield. FIG. 9 shows that the yield of carbon oxides is again much higher in the bubbling reactor than in the hybrid reactor. The difference of the carbon oxide yield between the bubbling reactor and the hybrid reactor is more than 5%. Thus, some of the propylene has been converted to other by-products. The model simulation shows that more acrolein will be produced in a hybrid reactor than in a bubbling reactor. The acrolein left in the reactor effluent can be recycled to the reactor to further increase the acrylonitrile yield since, as shown by the reaction mechanisms, acrolein can also be converted to acrylonitrile by reacting with ammonia.

The modeling results showed that a hybrid reactor can achieve about 5% higher acrylonitrile product yield for propylene ammoxidation when compared on a catalyst equivalent basis to the reaction zone arrangements. By recycling the acrolein from the hybrid reactor effluent, higher product yields can also be achieved. Although a circulating reactor can achieve very similar product yields, the catalyst circulating rate will be much higher and, therefore, more costly to operate.

What is claimed is:

1. An apparatus for the ammoxidation of propene to acrylonitrile by contact with a particulate catalyst, said apparatus comprising:

a first vessel defining a dense phase reaction zone having a first transverse flow area and at least one reactant inlet for receiving propylene and/or ammonia reactants;

an indirect heat exchange surface on the interior of the first vessel for indirectly cooling the dense bed reaction zone;

a second vessel defining a circulating fluidized bed (CFB) reaction zone having a second transverse flow area that is less than the first transverse flow area and having a reactant outlet;

a reducer for joining an outlet end of the first vessel with an inlet end of the second vessel and establishing a reactant and catalyst flow path from the first vessel through the reducer and the second vessel and out of the reactant outlet;

at least one oxygen injector for introducing an oxygen-containing stream into the reducer or the second vessel along the reactant and catalyst flow path;

at least one separator in communication with the reactant outlet to separate catalyst particles from a reactant stream; and, a separator outlet for delivering the reacted stream.

2. The apparatus of claim 1 wherein a plurality of injectors is spaced apart along the catalyst and reactant flow path for staged injection of the oxygen-containing stream.

3. The apparatus of claim 1 wherein a catalyst conduit communicates catalyst from the separator to a feed conduit that communicates with the inlet of the first reaction zone.

4. The apparatus of claim 3 wherein a third vessel contains the separator, the separator is in the form of multiple cyclone separators, and a reactant inlet housed in an upper portion of the third vessel communicates with the reactant inlet to discharge the reactant steam in the upper portion of a disengaging zone defined by the third vessel.

5. The apparatus of claim 1 wherein the separator has a catalyst outlet in direct communication with a third vessel and the third vessel has an indirect heat exchange surface within its interior for indirectly cooling catalyst.

6. The apparatus of claim 5 wherein the third vessel has at least one steam inlet for injecting steam into a dense catalyst bed located therein.

7. The apparatus of claim 1 wherein the second vessel comprises a transport conduit and a third vessel houses at least a portion of the transport conduit.

8. The apparatus of claim 7 wherein an external transfer conduit transfers the reactant mixture from the transport conduit to the third vessel.

9. An apparatus for controlling the temperature and limiting the backmixing of catalytic reactions, said apparatus comprising:

a first vessel defining a dense phase reaction zone having a first transverse flow area and at least one reactant inlet for receiving a plurality of reactants;

an indirect heat exchange surface on the interior of the first vessel for indirectly cooling the dense bed reaction zone;

a second vessel defining a circulating fluidized bed (CFB) reaction zone having a second transverse flow area that is less than the first transverse flow area and having a reactant outlet;

a reducer for joining an outlet end of the first vessel with an inlet end of the second vessel and establishing a reactant and catalyst flow path from the first vessel through the reducer and the second vessel and out of the reactant outlet;

at least one injector for introducing a reactant-containing stream into the reducer or the second vessel along the reactant and catalyst flow path;

at least one separator in communication with the reactant outlet to separate catalyst particles from a reactant stream; and a separator outlet for delivering the reacted stream.

10. The apparatus of claim 9 wherein a separation vessel receives the catalyst from the separator and catalyst transfer conduit provides at least a portion of catalyst recirculation system for returning catalyst to the reactant inlet.

11. The apparatus of claim 10 wherein a plurality of injection conduits transfer catalyst from the regenerator as the at least one injector for introducing catalyst as the reactant-containing stream into the reducer or the second vessel.

* * * * *